US012702798B2

(12) United States Patent
Tani et al.

(10) Patent No.: US 12,702,798 B2
(45) Date of Patent: Aug. 11, 2026

(54) STEERABLE CATHETER

(71) Applicants: NATIONAL UNIVERSITY CORPORATION SHIGA UNIVERSITY OF MEDICAL SCIENCE, Shiga (JP); ZEON CORPORATION, Tokyo (JP)

(72) Inventors: Tohru Tani, Shiga (JP); Atsushi Yamada, Shiga (JP); Tatsuya Shima, Tokyo (JP); Wataru Yonemichi, Tokyo (JP)

(73) Assignees: NATIONAL UNIVERSITY CORPORATION SHIGA UNIVERSITY OF MEDICAL SCIENCE, Shiga (JP); ZEON CORPORATION, Tokyo (JP)

( * ) Notice: Subject to any disclaimer, the term of this patent is extended or adjusted under 35 U.S.C. 154(b) by 785 days.

(21) Appl. No.: 17/593,619

(22) PCT Filed: Mar. 2, 2020

(86) PCT No.: PCT/JP2020/008720

§ 371 (c)(1), (2) Date: Sep. 21, 2021

(87) PCT Pub. No.: WO2020/195582

PCT Pub. Date: Oct. 1, 2020

(65) Prior Publication Data

US 2022/0152357 A1 May 19, 2022

(30) Foreign Application Priority Data

Mar. 22, 2019 (JP) ................................. 2019-055397

(51) Int. Cl.

*A61M 25/01* (2006.01)
*A61M 25/00* (2006.01)

(52) U.S. Cl.

CPC .... *A61M 25/0147* (2013.01); *A61M 25/0026* (2013.01); *A61M 25/0074* (2013.01); *A61M 25/008* (2013.01); *A61M 25/0136* (2013.01)

(58) Field of Classification Search

CPC ........ A61M 25/0147; A61M 2025/015; A61M 25/0074; A61M 25/008; A61M 25/0136;

(Continued)

(56) References Cited

U.S. PATENT DOCUMENTS 4,280,500 A 7/1981 Ono
8,473,023 B2 6/2013 Worley et al.

(Continued)

FOREIGN PATENT DOCUMENTS

CN 107148289 A 9/2017
JP H04-504368 A 8/1992

(Continued)

OTHER PUBLICATIONS

International Preliminary Report on Patentability issued in International Application No. PCT/JP2020/008720, issued on Sep. 28, 2021.

(Continued)

*Primary Examiner* — Lauren P Farrar
*Assistant Examiner* — Kathleen Paige Farrell
(74) *Attorney, Agent, or Firm* — Knobbe, Martens, Olson & Bear, LLP

(57) ABSTRACT

A steerable catheter includes a flexible tube having a distal end and a proximal end. The tube includes a first tube section (sheath body section) the flexibility of which does not substantially change even upon receiving compression force in the axial direction; and a second tube section (deflection section) joined so as to be continuous with the distal end of the first tube section and constituted by a porous tube becoming hard upon being compressed according to the (Continued)

(a)

(b)

(c)

(d)

degree of the compression force acting in the axial direction and returning to being soft when the compression force is released. The tube includes operation means (wires) for releasably exerting a compression force compressing the second tube section in the axial direction and a deflection force deflecting the second tube section. According to some embodiments, both operability and insertability of the steerable catheter can be improved.

4 Claims, 7 Drawing Sheets

(58) Field of Classification Search
CPC ...... A61M 2025/0161; A61M 25/0141; A61M 25/0133; A61M 25/0113; A61M 2025/09116; A61M 25/09041; A61M 29/00; A61B 2017/003; A61B 2017/00318; A61B 2034/301; A61B 1/0052
See application file for complete search history.

(56) References Cited

U.S. PATENT DOCUMENTS

| | | | | |
|---|---|---|---|---|
| 2004/0077929 | A1 | 4/2004 | Suyama et al. | |
| 2005/0010095 | A1* | 1/2005 | Stewart | A61B 18/1492 606/41 |
| 2010/0280449 | A1 | 11/2010 | Alvarez et al. | |
| 2016/0367787 | A1* | 12/2016 | Van Hoven | A61F 2/246 |
| 2017/0143936 | A1* | 5/2017 | Sliwa | A61M 25/0133 |
| 2017/0354463 | A1* | 12/2017 | Mori | A61M 25/0147 |
| 2018/0344981 | A1* | 12/2018 | Laduca et al. | A61M 25/0147 |

FOREIGN PATENT DOCUMENTS

| | | |
|---|---|---|
| JP | H05-115426 A | 5/1993 |
| JP | H10(1998)-033688 | 2/1998 |
| JP | 2002-272675 | 9/2002 |
| JP | 2003-525092 | 8/2003 |
| JP | 2014-514095 | 6/2014 |
| JP | 2014-188039 | 10/2014 |
| JP | 2015-530223 | 10/2015 |
| KR | 10-2018-0106612 | 10/2018 |
| KR | 10-2018-0106612 A | 10/2018 |
| WO | WO 1990/007355 A1 | 7/1990 |
| WO | WO 01/64278 | 9/2001 |
| WO | WO 2012/098788 A1 | 7/2012 |
| WO | WO 2012/142540 | 10/2012 |
| WO | WO 2014/055547 | 4/2014 |
| WO | WO 2016/044211 A1 | 3/2016 |
| WO | WO 2017/158069 A1 | 9/2017 |

OTHER PUBLICATIONS

Office Action issued in Chinese Application No. 202080016125.7, dated Sep. 7, 2022.

International Search Report, dated Apr. 21, 2020, issued in International Application No. PCT/JP2020/008720.

Extended European Search Report issued in EP Application No. 20779139.3, dated Nov. 28, 2022.

Extended European Search Report issued in EP Application No. 24171078.9, dated Jul. 16, 2024.

Office Action issued in Japanese Application No. 2024-108115, dated May 7, 2025.

* cited by examiner (a)

(b)

(c)

(d)

STEERABLE CATHETER

TECHNICAL FIELD

The present invention relates to a catheter as a medical treatment tool used for various treatments, examinations, and so on and, more particularly, to a steerable catheter having a freely deflectable tip section or the like.

BACKGROUND ART

A steerable catheter is known as a medical treatment tool (e.g. catheter for contrast medium injection, electrode catheter, ablation catheter, and catheter sheath) inserted into a target tissue such as various organs (e.g. bile duct and heart) through a body cavity, a lumen, a blood vessel, or the like. In order to, for example, facilitate the insertion and access to the target tissue, the orientation of the tip (distal end) of the catheter inserted into the body can be deflected by operating an operation section provided on the base end (proximal end) side of the catheter disposed outside the body (see, for example, Patent Document 1 and Patent Document 2).

The catheter described in Patent Document 1 is an endoscopic catheter used for, for example, injecting an X-ray contrast medium into a bile duct for examination in the bile duct. The catheter is inserted into the duodenum via an endoscope. Then, the tip section of the catheter can be deflected (curved) by operating (pushing or pulling) an operation wire from the outside of the body such that the tip section is inserted into the duodenal papilla from the duodenum side and easily reaches the inside of the bile duct. The catheter described in Patent Document 1 has a lumen into which the operation wire for deflecting the tip section is inserted in addition to a large-diameter lumen used for contrast medium injection or the like. The operation wire is joined to a pointed tip provided in the tip section of the catheter by means such as plasma welding. Accordingly, the tip section of the catheter can be deflected by pulling the operation wire on the outside of the body.

The tip-steerable catheter described in Patent Document 2 is used for, for example, guiding an ablation catheter to a cardiac site to be treated so that catheter ablation treatment is performed on the heart. The tip section of the catheter can be deflected (curved) by operating an operation section from the outside of the body such that the tip of the ablation catheter is easily guided to a desired cardiac position. A catheter tube constituting the catheter described in Patent Document 2 has a pair of wire lumens at positions in the tube wall thereof facing each other at 180° in addition to a main lumen into which various treatment tools are inserted. Further, the rigidity of the part to be deflected in the tip section of the catheter tube is set to, for example, decrease in stages toward the tip, the tips of a pair of wires respectively inserted through the wire lumens are connected to a ring (pull ring) integrally mounted on the tip section by means such as laser welding, and the base ends of the pair of wires are connected to the operation section. Further, by operating the operation section, one wire is pulled, the other wire is loosened, and the orientation of the tube tip can be controlled.

By the way, a steerable section (deflection section) in this type of steerable catheter needs to be flexible enough to be easily and freely deflected (curved) as a result of wire operation. However, when the configuration is flexible (soft) in view of operability, bending or buckling may occur and a decline in insertability may arise in the case of, for example, breaking through (penetrating) a stenosed section in a lumen such as a bile duct. In contrast, the operability may be sacrificed when the configuration is rigid (hard) in view of the insertability.

CITATION LIST

Patent Document

Patent Document 1: JP 2002-272675 A
Patent Document 2: JP 2014-188039 A

SUMMARY OF THE INVENTION

Problem to be Solved by the Invention

The present invention has been made in view of such circumstances, and an object of the present invention is to provide a steerable catheter with which both operability and insertability can be improved.

Means for Solving Problem

The steerable catheter according to the present invention for achieving the above object is a steerable catheter comprising a flexible tube having a distal end inserted into a body and a proximal end disposed outside the body, wherein the tube includes a first tube section having a property hardly to change a flexibility even upon receiving compression force in an axial direction and a second tube section joined so as to be continuous with a distal end of the first tube section, and constituted by a porous tube able to be hard upon being compressed according to a degree of the compression force acting in the axial direction and able to be return to being soft when the compression force is released, and the catheter includes operation means for releasably exerting a compression force compressing the second tube section in the axial direction and a deflection force deflecting the second tube section.

According to the steerable catheter according to the present invention, the second tube section can be deflected by appropriately operating the operation means and applying the deflection force to the second tube section with as little compression force as possible acting on the second tube section and the second tube section maintained soft. At this time, the second tube section is soft, and thus satisfactory operability can be realized. Meanwhile, in the case of, for example, breaking through (penetrating) a stenosed section in a lumen in the body such as a bile duct, bending or buckling can be suppressed by appropriately operating the operation means and hardening the second tube section by applying the compression force and the insertability can be improved. Accordingly, a steerable catheter with which both operability and insertability can be improved can be provided.

In the steerable catheter according to the present invention, the tube is capable of including at least three wire lumens mutually spaced apart in a tube wall of the tube and extending from a proximal end section of the tube to a distal end section of the tube, and the operation means is capable of including at least two wires, substantially half on one end section side thereof is inserted through one of the wire lumens, an intermediate part thereof is folded back on a distal end section of the second tube section, substantially half on the other end section side thereof is inserted through another one of the wire lumens, and the one and the other end sections thereof reach a proximal end of the first tube section. The second tube section can be hardened by pulling both end sections (one and the other end sections) of all the wires (or some of the wires that are appropriate depending on the wire lumen disposition) with the same tensile force between the wires such that the compression force acts on the second tube section. In addition, by pulling (or pulling only some of the wires) with a difference in tensile force between the wires such that the deflection force acts on the second tube section, the second tube section can be deflected in accordance with the difference in tensile force.

In the steerable catheter according to the present invention, the tube is capable of including at least three wire lumens mutually spaced apart in a tube wall of the tube and extending from a proximal end section of the tube to a distal end section of the tube, and the operation means is capable of including at least three wires, each having a distal end connected to a distal end section of the second tube section, inserted through one of the wire lumens, and having a proximal end reaching a proximal end of the first tube section. The second tube section can be hardened by pulling the proximal ends of all the wires (or some of the wires that are appropriate depending on the wire lumen disposition) with the same tensile force between the wires such that the compression force acts on the second tube section. In addition, by pulling (or pulling only some of the wires) with a difference in tensile force between the wires such that the deflection force acts on the second tube section, the second tube section can be deflected in accordance with the difference in tensile force.

MODE(S) FOR CARRYING OUT THE INVENTION

Figure 1:
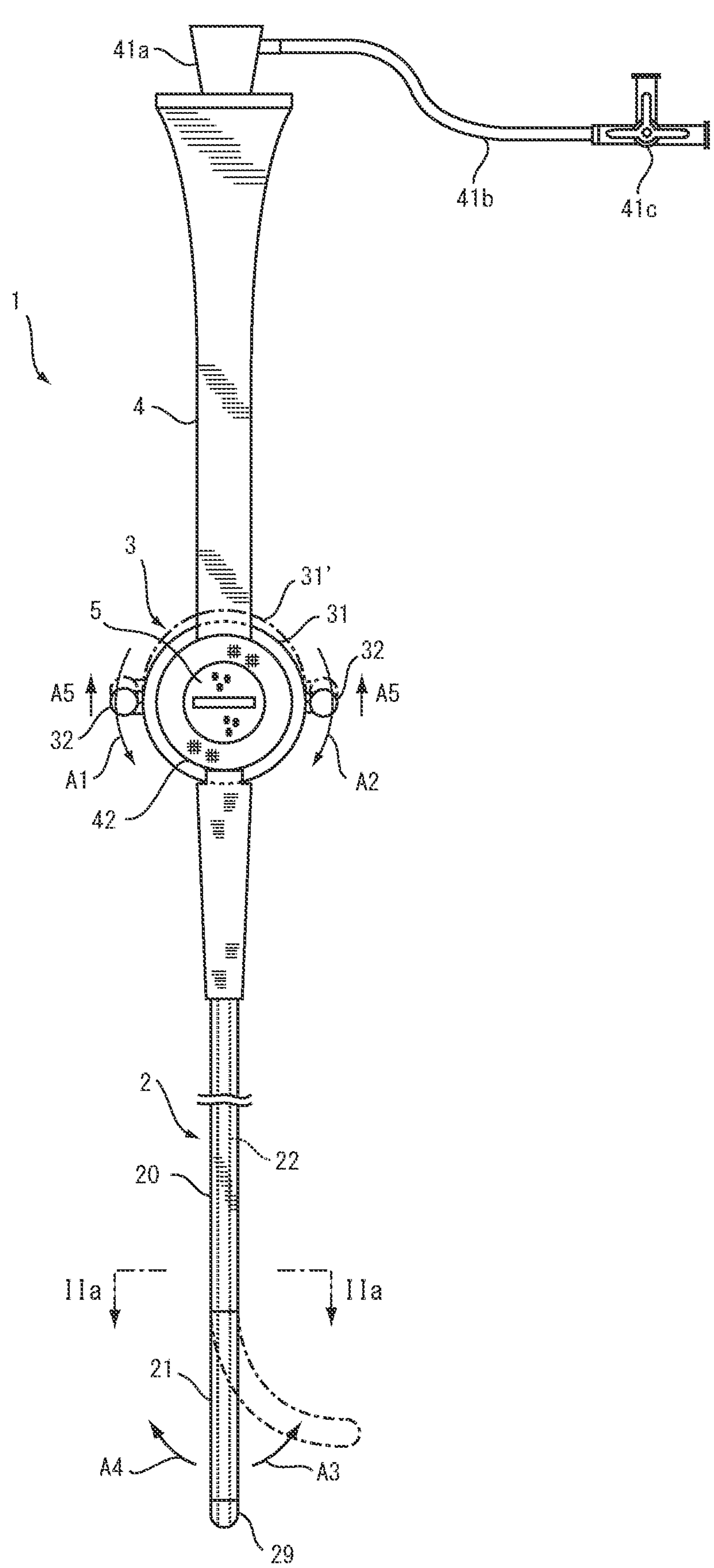
FIG. 1 is a diagram illustrating an external configuration of the steerable catheter according to an embodiment of the present invention.
Figure 2A:
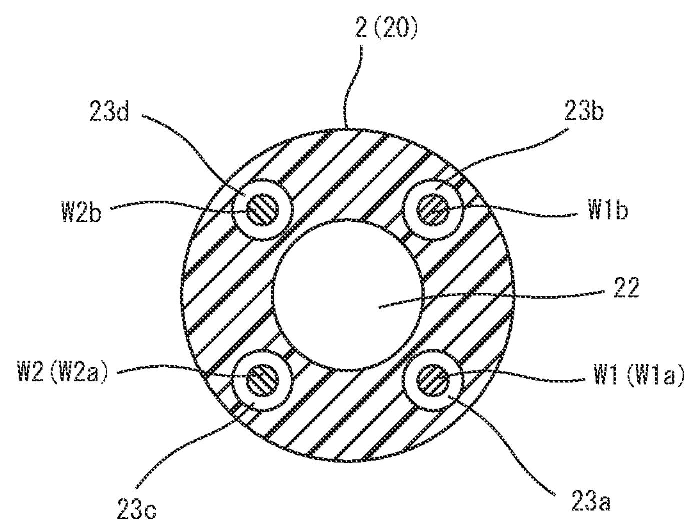
FIG. 2A is a cross-sectional view taken along line IIa-IIa of FIG. 1.
Figure 2B:
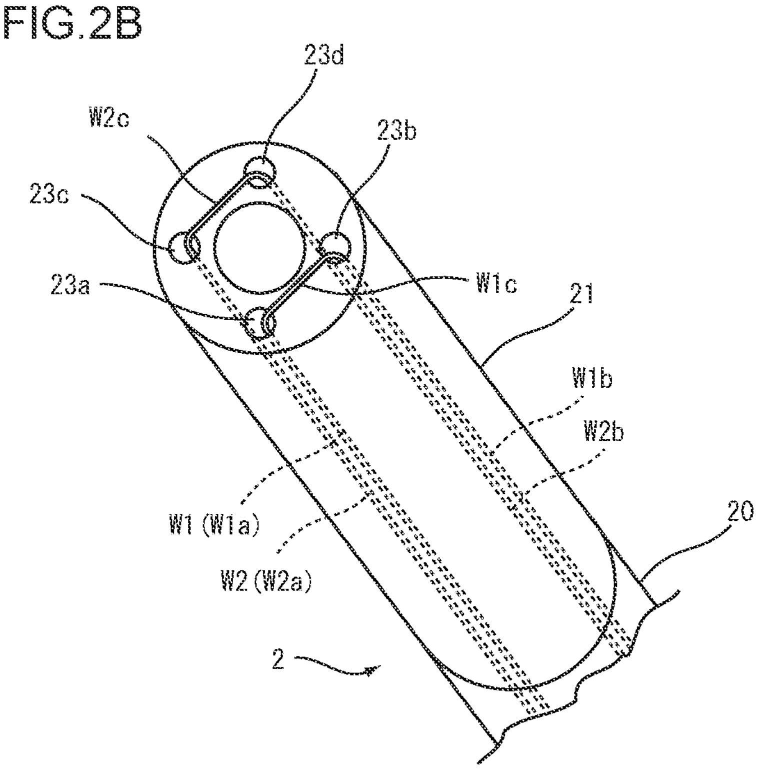
FIG. 2B is an enlarged perspective view illustrating a main part of the steerable catheter of FIG. 1.
Figure 2C:
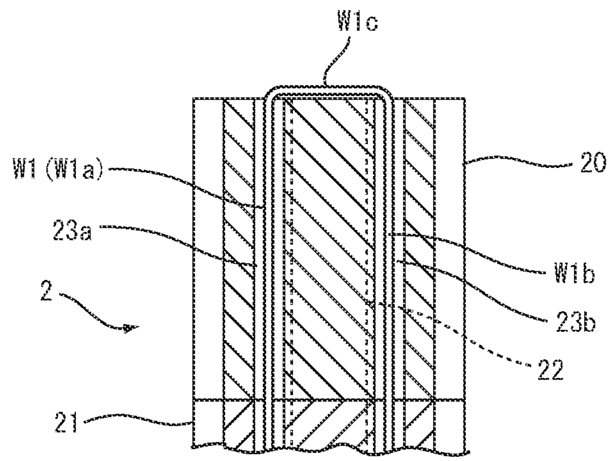
FIG. 2C is a cross-sectional view of the distal end section of the steerable catheter of FIG. 2B cut along a plane passing through the respective axes of a pair of wire lumens.

Hereinafter, an embodiment of the present invention will be specifically described with reference to the drawings. The catheter sheath (steerable sheath) as the steerable catheter of the present embodiment is a catheter inserted in advance of an electrode catheter for electrocardiographic detection, an ablation catheter for cauterizing an affected area, or the like when, for example, catheter ablation is performed and guiding the electrode catheter, the ablation catheter, or the like. Although the catheter sheath will be described below as an example of the steerable catheter to which the present invention is applied, the present invention can also be applied to an electrode catheter, an ablation catheter, a steerable endoscopic catheter used for, for example, injecting an X-ray contrast medium into a bile duct for examination in the bile duct, and other steerable catheters.

It should be noted that the catheter ablation is a treatment method for cardiac arrhythmia treatment by which an ablation catheter having a high-frequency electrode in its tip section is inserted and reaches the myocardial tissue that has caused the intracardiac arrhythmia via a blood vessel, the myocardial tissue or its vicinity is cauterized at approximately 60 to 70° C., coagulative necrosis is caused, and the arrhythmia circuit is broken.

First, see FIGS. 1 and 2A to 2C. A catheter sheath (steerable catheter) 1 is configured to substantially include a sheath (tube) 2, an operation section 3, a grip section 4, and a pair of wires (operation means) W1 and W2.

The sheath 2 is made of a flexible hollow tube having a distal end inserted into a body and a proximal end disposed outside the body and is constituted by a sheath body section (first tube section) 20 disposed on the proximal end side and a deflection section (second tube section) 21 disposed on the distal end side. The sheath body section 20 is configured to have relatively high rigidity such that its flexibility does not substantially change even upon receiving compression force in the direction along its axis (axial direction). A multilayer tube including a braid layer made of reticulated stainless steel or the like and a plurality of resin layers is used as the sheath body section 20.

The deflection section 21 is integrally joined such that its proximal end is continuous with the distal end of the sheath body section 20. The lumen of the deflection section 21 and the lumen of the sheath body section 20 are continuously connected to each other and constitute a main lumen 22. The deflection section 21 is constituted by a porous tube becoming hard upon being compressed according to the degree of the compression force acting in the axial direction and returning to being soft when the compression force is released. The flexibility of the porous tube can be controlled by adjusting the compression force acting in the axial direction.

Although the material of the sheath body section 20 is not particularly limited insofar as it has flexibility, the material is preferably a thermoplastic resin or a thermoplastic elastomer and polyamide-based elastomer such as polyether block amide copolymer, polyamide, polyimide, polyamide-imide, polyethylene terephthalate, polyethylene, polypropylene, polyurethane, ethylene-vinyl acetate copolymer, polyvinyl chloride, polytetrafluoroethylene, tetrafluoroethylene-hexafluoropropylene copolymer, tetrafluoroethylene-perfluoroalkyl vinyl ether copolymer, or the like is used.

Although the material of the porous tube constituting the deflection section 21 is not limited, using polytetrafluoroethylene (PTFE) is preferable in that, for example, it is excellent in heat resistance, chemical resistance, weather resistance, water repellency, and so on. A tube manufactured by axially stretching a tube obtained by performing extrusion molding on PTFE can be used as the porous tube. By making the PTFE porous, the required waterproofness can be obtained and breathability can be retained at the same time. In addition, the porosity can be adjusted and the change in flexibility during compression can be appropriately adjusted (controlled) by appropriately adjusting the stretching rate (degree of stretching) during the stretching. It should be noted that the ventilation performance can also be changed by adjusting the porosity.

An insertion hole through which the proximal end-side part of the sheath 2 is inserted is formed in the operation section 3 and the grip section 4 attached to the proximal end side of the sheath 2, and a sheath hub 41*a* is attached to the proximal end of the grip section 4.

The sheath hub 41*a* has a lumen, and the sheath 2 in the grip section 4 is attached to the proximal end side of the sheath hub 41*a* such that the lumen of the sheath hub 41*a* and the main lumen 22 of the sheath 2 communicate with each other. In addition, a catheter insertion port provided with a hemostatic valve is formed on the distal end side of the sheath hub 41*a*. When the catheter sheath 1 is used (during treatment), the electrode catheter and the ablation catheter described above are inserted from the catheter insertion port of the sheath hub 41*a* and guided to the main lumen 22 of the sheath 2 and the distal end section of each is guided to the myocardial tissue to be treated. In addition, a side injection tube is formed in the side section of the sheath hub 41*a* and a three-way stopcock 41*c* is attached to the side injection tube via a tube 41*b*. A syringe or the like can be attached to the three-way stopcock 41*c*, and then blood can be suctioned out of the body or a drug solution can be sent into the body.

A substantially cylindrical tip protection member 29 made of resin and having a hemispherical distal end side is provided at the distal end of the sheath 2 (tip of the deflection section 21). The tip protection member 29 has a lumen substantially equal in diameter to the main lumen 22 of the sheath 2 and is integrally joined (fixed) to the distal end section of the sheath 2 (deflection section 21) by heat fusion or the like. However, the tip protection member 29 may be omitted.

Four wire lumens (sub-lumens) 23*a* to 23*d* substantially parallel to the main lumen 22 are formed in the tube wall of the sheath 2 (sheath body section 20 and deflection section 21) so as to surround the outside of the main lumen 22. The wire lumens 23*a* to 23*d* are formed from the proximal end section of the sheath 2 (proximal end section of the sheath body section 20) to the distal end section (distal end section of the deflection section 21). The wire lumens 23*a* to 23*d* are formed on the outside of the main lumen 22 with the axis of the sheath 2 as the center and separated from each other at an angular pitch (angular interval) of approximately 90°.

The single wire W1 is inserted through the wire lumen 23*a* and the wire lumen 23*b*, and the single wire W2 is inserted through the wire lumen 23*c* and the wire lumen 23*d*. Although the wires W1 and W2 are formed of a metal such as stainless steel in the present embodiment, the wires W1 and W2 may be formed of another material such as resin.

The wire W1 is disposed such that substantially half W1*a* on one end section side thereof is inserted through the wire lumen 23*a*, an intermediate part W1*c* thereof is folded back on the distal end surface to which the tip protection member 29 of the sheath 2 is joined, substantially half W1*b* on the other end section side thereof is inserted through the wire lumen 23*b*, and both end sections (one and the other end sections) thereof are positioned in the operation section 3 on the proximal end side of the sheath 2. Likewise, the wire W2 is disposed such that substantially half W2*a* on one end section side thereof is inserted through the wire lumen 23*c*, an intermediate part W2*c* thereof is folded back on the distal end surface to which the tip protection member 29 of the sheath 2 is joined, substantially half W2*b* on the other end section side thereof is inserted through the wire lumen 23*d*, and both end sections (one and the other end sections) thereof are positioned in the operation section 3 on the proximal end side of the sheath 2.

Both end sections of the wire W1 and both end sections of the wire W2 are pulled out of side holes provided in the sheath 2 in the operation section 3 provided on the proximal end side of the sheath 2 and are respectively connected to the operation section 3 (a rotational operation member 31). The operation section 3 has a pair of protrusion-shaped gripping portions 32 and 32 integrally provided on the rotational operation member 31 and is held by a holding section 42 provided on the tip (distal end) side of the grip section 4 via a screw-in-type knob member 5.

The rotational operation member 31 is held by the holding section 42 so as to be capable of sliding by a predetermined amount to the proximal end side as indicated by the one-dot chain line with reference numeral 31' in FIG. 1 by pressing both of the pair of gripping portions 32 and 32 to the proximal end side as indicated by arrows A5 in FIG. 1. The rotational operation member 31 is urged by urging means (not illustrated) so as to return to its original position when the pressing in the arrow A5 direction is released.

Figure 3:
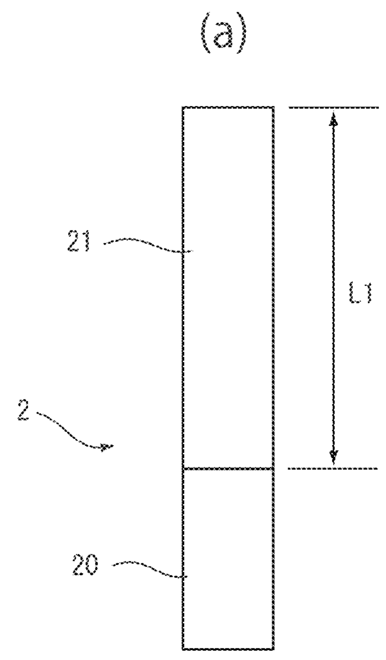
FIGS. 3A to 3D are enlarged views illustrating the distal end section of the steerable catheter of FIG. 1 and diagrams for describing the operation of a deflection section.
Figure 3:
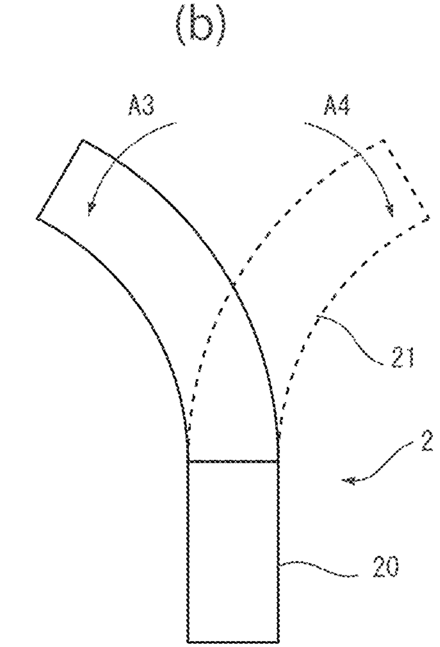
Figure 3:
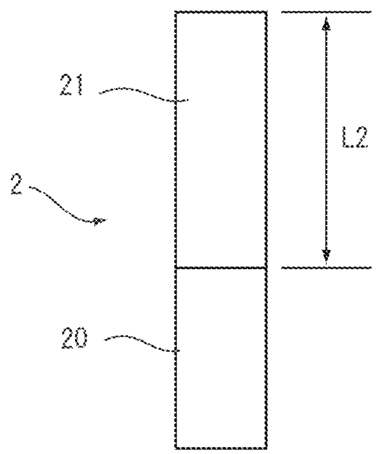
Figure 3:
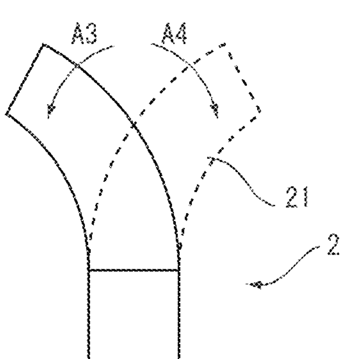

In the neutral state illustrated in FIG. 1, both the wire W1 and the wire W2 are substantially tension-less and the deflection section 21 at the tip of the sheath 2 is in a state of linear extension as illustrated in FIGS. 1 and 3A. At this time, no compression force acts on the deflection section 21 in the axial direction, and thus the deflection section 21 has an axial dimension of L1 without being compressed and is relatively soft owing to the properties of the porous tube constituting the deflection section 21.

When the rotational operation member 31 is rotated in the direction of an arrow A1 in FIG. 1 by operating the gripping portions 32 and 32 of the rotational operation member 31 in the neutral state, the wire W1 is pulled, the wire W2 is loosened, and the deflection section 21 at the tip is deflected as a result as indicated by an arrow A3 in FIGS. 1 and 3B.

In contrast, when the rotational operation member 31 is rotated in the arrow A2 direction in FIG. 1 by operating the gripping portions 32 and 32 of the rotational operation member 31, the wire W1 is loosened, the wire W2 is pulled, and the deflection section 21 at the tip is deflected as a result as indicated by an arrow A4 in FIGS. 1 and 3B.

In a case where it is desired to fix the shape of the deflection section 21 with the deflection section 21 deflected, the rotational operation member 31 is pressed against the holding section 42 by the knob member 5 being rotated clockwise and tightened. Then, the rotational operation member 31 is fixed at the current position and the shape of the deflection section 21 is fixed. In a case where it is desired to release the fixing of the shape of the deflection section 21 (adjust the deflection state), the rotational operation member 31 is loosely pressed against the holding section 42 by the knob member 5 being rotated counterclockwise and loosened contrary to the above. Then, the rotational operation member 31 becomes rotatable. As a result, the fixing of the shape of the deflection section 21 is released and the deflection state of the deflection section 21 can be adjusted by gripping the gripping portion 32 and rotating the rotational operation member 31.

Next, the rotational operation member 31 slides by a predetermined amount to the proximal end side when both the gripping portions 32 and 32 are pressed to the proximal end side against the urging force of the urging means (not illustrated) in the neutral state illustrated in FIG. 1 and as indicated by the arrows A5 in FIG. 1. In this state, both the wires W1 and W2 are pulled substantially evenly to the proximal end side (with the same tensile force) and become tense. As a result, a force attributable to the tense wires W1 and W2 acts on the distal end of the deflection section 21. In other words, the proximal end of the deflection section 21 is substantially restrained by the distal end of the sheath body section 20 (does not move to the proximal end side), and thus compression force acts on the deflection section 21 in the axial direction owing to the pulling force of the wires W1 and W2 to the proximal end side. Owing to this compression force, the deflection section 21 is compressed (shortened) in the direction along the axis, the axial dimension of the deflection section 21 becomes L2 smaller than L1 as illustrated in FIG. 3C, and the deflection section 21 becomes relatively hard in accordance with the properties of the porous tube constituting the deflection section 21.

When the pressing force on the gripping portions 32 and 32 is released, the rotational operation member 31 can be slid to the original position (neutral position) on the distal end side by the urging force of the urging means (not illustrated) and returned to being relatively soft. In a case where it is desired to maintain this with the deflection section 21 relatively hard, the knob member 5 is rotated clockwise and tightened. Then, the rotational operation member 31 is pressed against the holding section 42 and the rotational operation member 31 is fixed at the current position. In a case where it is desired to release this (make it soft or adjust the deflection state), the knob member 5 is rotated counterclockwise and loosened contrary to the above. Then, the rotational operation member 31 is loosely pressed against the holding section 42 and the rotational operation member 31 can be returned to the original position (neutral position).

It should be noted that deflection in a state of compression, if necessary, is also possible as illustrated in FIG. 3D by rotating the rotational operation member 31 with the rotational operation member 31 slid to the proximal end side and the deflection section 21 hard. In addition, compression and hardening can also be performed as illustrated in FIG. 3D by sliding the rotational operation member 31 to the proximal end side after the deflection section 21 is appropriately deflected by rotating the rotational operation member 31 at the neutral position (that is, in a state where the deflection section 21 is soft). In addition, if necessary, the flexibility of the deflection section 21 can also be changed and controlled by appropriately adjusting the amount of sliding when the rotational operation member 31 is slid from the neutral position to the proximal end side.

In the embodiment described above, the sheath 2 as the deflection section 21 is constituted by the sheath body section 20 and the deflection section 21, the flexibility of the sheath body section 20 does not substantially change even upon receiving compression force in the axial direction, and the deflection section 21 is joined so as to be continuous with the distal end of the sheath body section 20 and constituted by the porous tube becoming hard upon being compressed according to the degree of the compression force acting in the axial direction and returning to being soft when the compression force is released. Further, the wires W1 and W2 inserted through the plurality of wire lumens 23*a* to 23*d* of the sheath 2 releasably exert a compression force compressing the deflection section 21 in the axial direction and a deflection force deflecting the deflection section 21.

As a result, the deflection section 21 can be deflected by pulling one of the wires W1 and W2 to the proximal end side with the wires W1 and W2 neutral and the deflection section 21 maintained soft without compression force acting thereon. At this time, the deflection section 21 is soft, and thus satisfactory operability can be realized. Meanwhile, in the case of, for example, breaking through (penetrating) a stenosed section in a lumen in the body such as a bile duct, bending or buckling may occur and the insertion may become difficult with the deflection section 21 soft. In this case, compression force can be applied to the deflection section 21 and the deflection section 21 can become hard by pulling both the wires W1 and W2 to the proximal end side with the same tensile force. Accordingly, the occurrence of bending or buckling in the deflection section 21 can be reduced and the insertability of the catheter can be improved.

In addition, in the embodiment described above, the pair of wires W1 and W2 exert both the deflection force for deflecting the deflection section 21 and the compression force for compressing the deflection section 21. Accordingly, the configuration can be simplified as compared with a case where each is realized by separate means such as providing a wire for deflection force application and a wire for compression force application. However, it is a matter of course that each may be realized by separate means. For example, a compression tube having an outer diameter slightly smaller than the inner diameter of the main lumen 22 may be slidably inserted through the lumen (main lumen 22) of the sheath 2 (sheath body section 20 and deflection section 21) as means for applying compression force and the compression force may be applied to the deflection section 21 by connecting the distal end of the compression tube to the distal end of the deflection section 21 and pulling the compression tube to the proximal end side with respect to the sheath 2. It should be noted that the function as the main lumen in this case is borne by the lumen of the compression tube.

Further, in the embodiment described above, the substantially half W1*a* on one end section side of the wire W1 is inserted through the wire lumen 23*a*, the substantially half W1*b* on the other end side is inserted through the wire lumen 23*b*, the substantially half W2*a* on one end section side of the wire W2 is inserted through the wire lumen 23*c*, and the substantially half W2*b* on the other end side is inserted through the wire lumen 23*d*. Each of the wires W1 and W2 is folded back in the distal end section of the deflection section 21, and thus the number of components can be reduced as there is no need to provide a wire fixing member such as a pointed tip and a pull ring and manufacturing man-hours can be reduced as there is no need to mount a wire fixing member on the catheter tube or connect a wire to the member. In addition, the structural limitation of the catheter sheath 1 can be reduced and, for example, the opening area of the distal end (tip) of the sheath 2 (main lumen 22) can be increased as there is no need to secure a region for providing a wire fixing member in the structure of the catheter sheath 1.

In addition, the deflection force for deflecting the deflection section 21 is applied by pulling both the substantially half W1*a* inserted through the wire lumen 23*a* of the wire W1 and the substantially half W1*b* inserted through the wire lumen 23*b*. Accordingly, the force can be applied to a relatively wide range in the circumferential direction of the sheath 2 in accordance with the interval (angular interval) between the wire lumen 23*a* and the wire lumen 23*b*. The same applies to the wire W2. As a result, the force applied to the wire is smaller than in a case where the deflection operation is performed by pulling a single wire inserted through a single lumen without folding back, and thus the risk of wire breakage attributable to the deflection operation is reduced. In addition, the blurring of the distal end section during the deflection of the deflection section 21 can be reduced and a stable deflection can be realized. For the same reason, compression force can also be stably applied to the deflection section 21.

However, it is a matter of course that one wire may be inserted through each of the wire lumens 23*a* to 23*d*, that is, four wires may be provided and the distal end of each wire may be connected to the distal end of the deflection section 21 in an alternative configuration. In this case, the wire lumens may be three or five or more in number and the wires may be three or five or more in number.

Figure 4A:
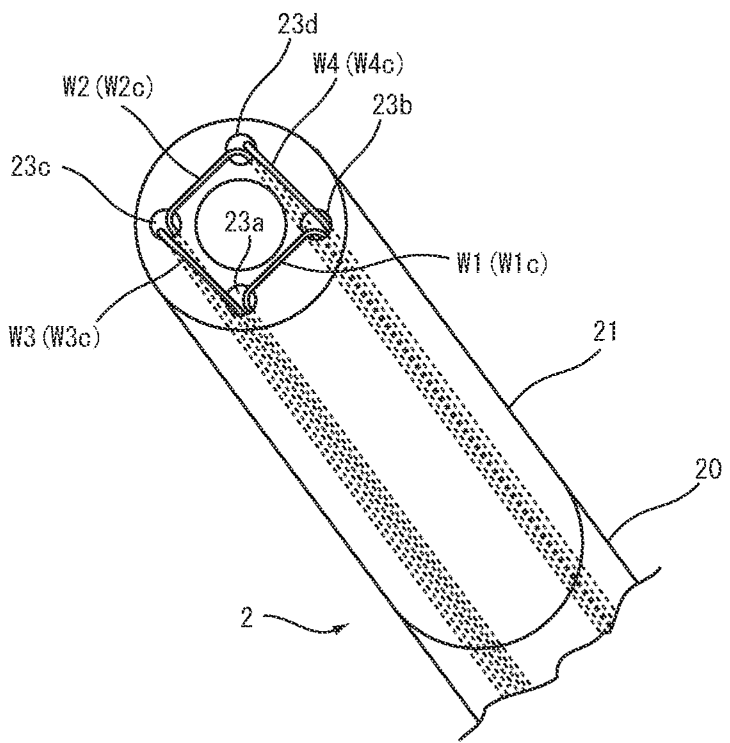
FIG. 4A is a perspective view illustrating a case where the number of wires inserted through the wire lumen of the steerable catheter of FIG. 2B is increased.
Figure 4B:
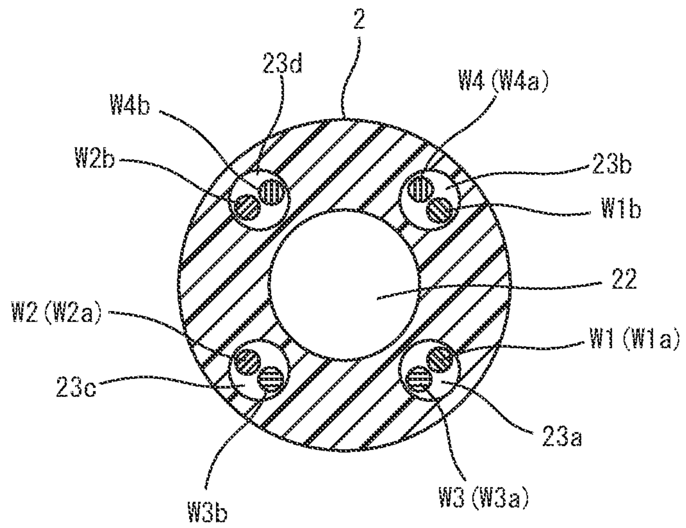
FIG. 4B is a cross-sectional view of the distal end section of the steerable catheter of FIG. 4A cut along a plane orthogonal to the axis thereof.
Figure 4C:
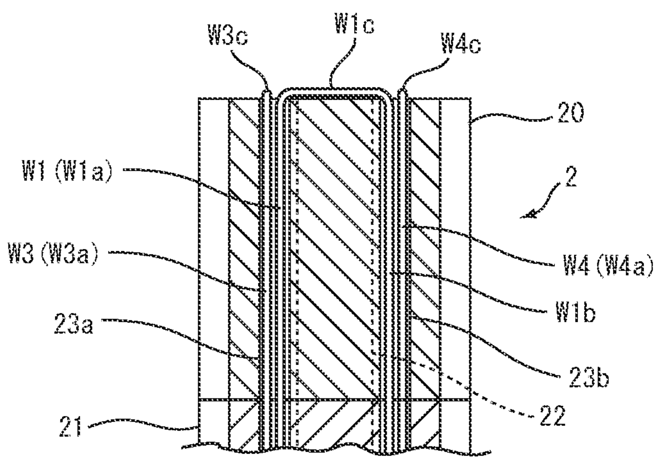
FIG. 4C is a cross-sectional view of the distal end section of the steerable catheter of FIG. 4A cut along a plane passing through the respective axes of a pair of wire lumens.

Although the two wires of the wire W1 inserted through the wire lumen 23*a* and the wire lumen 23*b* and the wire W2 inserted through the wire lumen 23*c* and the wire lumen 23*d* are used in the embodiment described above, four wires may be used in an alternative configuration with a wire W3 and a wire W4 added as illustrated in FIGS. 4A to 4C.

In other words, as for the wire W3, substantially half W3*a* on one end section side thereof is inserted through the wire lumen 23*a*, an intermediate part W3*c* thereof is folded back on the distal end surface to which the tip protection member 29 of the sheath 2 is joined, and substantially half W3*b* on the other end section side thereof is inserted through the wire lumen 23*c*. As for the wire W4, substantially half W4*a* on one end section side thereof is inserted through the wire lumen 23*b*, an intermediate part W4*c* thereof is folded back on the distal end surface to which the tip protection member 29 of the sheath 2 is joined, and substantially half W4*b* on the other end section side thereof is inserted through the wire lumen 23*d*. With this configuration, deflection can be performed in four directions by appropriately selecting and pulling one of the wires W1 to W4. In addition, the deflection section 21 can be deflected in any direction by 360° by appropriately selecting a combination of two adjacent wires out of the wires W1 to W4 and adjusting the balance of the forces pulling the two. Further, the deflection section 21 can be hardened by pulling all of the wires W1 to W4 or the wires W1 and W2 or the wires W3 and W4 evenly (with the same tensile force). It should be noted that the configuration of the operation section 3 needs to be appropriately changed in response to the addition of the wires W3 and W4, examples of which include adding another rotational operation member similar to the rotational operation member 31 in the operation section 3.

Figure 5A:
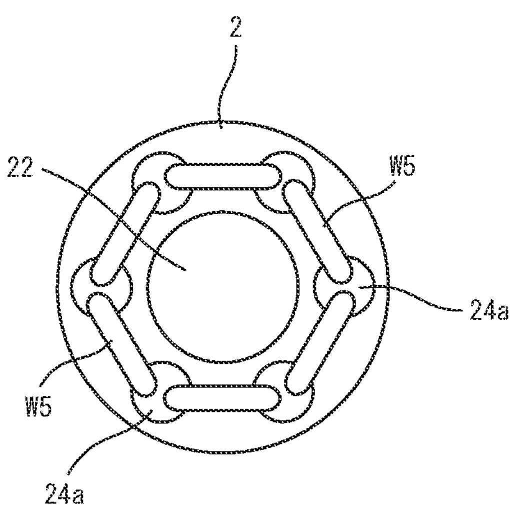
FIG. 5A is a diagram illustrating a modification example of the steerable catheter of FIG. 4A.
Figure 5B:
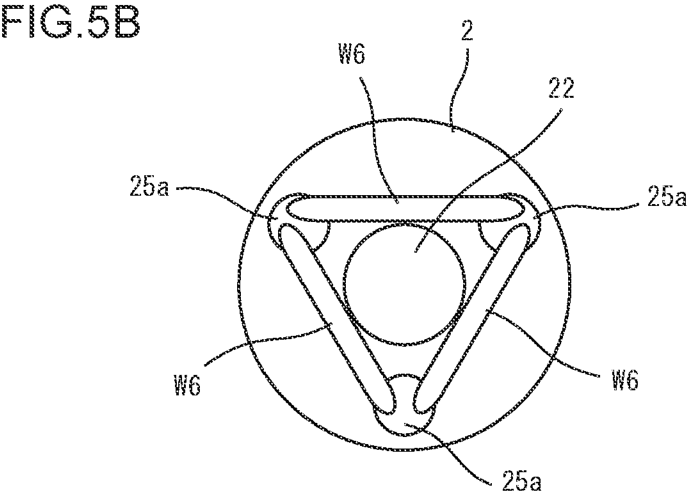
FIG. 5B is a diagram illustrating another modification example of the steerable catheter of FIG. 4A.
Figure 5C:
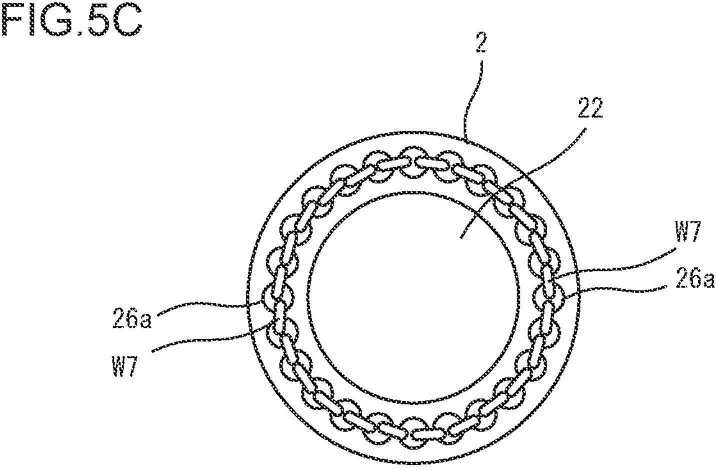
FIG. 5C is a diagram illustrating still another modification example of the steerable catheter of FIG. 4A.

In addition, although a case where the four wire lumens 23*a* to 23*d* are provided and the four wires W1 to W4 are provided has been described in the example illustrated in FIGS. 4A to 4C, the wire lumens can be increased or decreased in number and the wires can be accordingly increased or decreased in number as illustrated in, for example, FIGS. 5A to 5C.

In other words, in FIG. 5A, six wires W5 are provided with six wire lumens 24*a* provided at an angular pitch of 60°. As a result, in a case where the wires W5 are pulled one by one, the deflection section 21 can be deflected in six directions and the deflection section 21 can be deflected in any direction by 360° by appropriately selecting a combination of two adjacent wires W5 and adjusting the balance of the forces pulling the two. In FIG. 5B, three wires W6 are provided with three wire lumens 25*a* provided at an angular pitch of 120°. As a result, in a case where the wires W6 are pulled one by one, the deflection section 21 can be deflected in three directions and the deflection section 21 can be deflected in any direction by 360° by appropriately selecting a combination of two adjacent wires W6 and adjusting the balance of the forces pulling the two. In FIG. 5C, 24 wires W7 are provided with 24 wire lumens 26*a* provided at an angular pitch of 15°. As a result, the deflection section 21 can be deflected in 24 directions in a case where the wires W7 are pulled one by one. These are examples, the wire lumens may be three or more in number, and the wires may be two or more in number.

Although the wire lumens and the wires are equal in number to each other in the examples illustrated in FIGS. 5A to 5C, the numbers may be different from each other and, for example, the wires may be smaller in number than the wire lumens. In addition, although both end sections of a wire are inserted through a pair of adjacent wire lumens in the examples illustrated in FIGS. 5A to 5C, a pair of wire lumens may be, for example, intermittently selected and both end sections of a wire may be inserted therethrough.

The embodiment described above is to facilitate the understanding of the present invention without limiting the present invention. Accordingly, each element disclosed in the embodiment described above is intended to include every change in design and equivalent pertaining to the technical scope of the present invention.

EXPLANATIONS OF LETTERS OR NUMERALS

1 CATHETER SHEATH (STEERABLE CATHETER)
2 SHEATH (TUBE)
20 SHEATH BODY SECTION (FIRST TUBE SECTION)
21 DEFLECTION SECTION (SECOND TUBE SECTION)
22 MAIN LUMEN
23*a* TO 23*d* WIRE LUMEN
29 TIP PROTECTION MEMBER
3 OPERATION SECTION
31 ROTATIONAL OPERATION MEMBER
32 GRIPPING PORTION
4 GRIP SECTION
42 HOLDING SECTION
5 KNOB MEMBER
W1 TO W7 WIRE (OPERATION MEANS)

What is claimed is:

1. A steerable catheter comprising a flexible tube having a distal end and a proximal end, wherein:

the tube includes a first tube section having a high rigidity against a compression force in an axial direction and a second tube section joined so as to be continuous with a distal end of the first tube section, and the second tube section being constituted by a porous tube, in a neutral state in which no compression force is applied to the second tube section, the second tube section has a second axial dimension defined along a longitudinal axis, and in a compressed state in which a compression force is applied to the second tube section, the second tube section is compressed to a first axial dimension defined along the longitudinal axis, the first axial dimension being smaller than the second axial dimension, and the catheter operation means for applying the compression force along the longitudinal axis to the second tube section to shorten and harden the second tube section, and releasing the compression force so that the second tube section softens and returns to the neutral state, the operation means for applying and releasing the compression force in a repeated manner, the operation means for applying a deflection force, different from and independent of the compression force, to deflect the second tube section;

the steerable catheter further comprising a rotational member; and a pair of gripping portions operatively coupled to the rotational member, wherein one of the gripping portions is configured to be rotated to apply the deflection force, wherein both of the gripping portions are configured to be simultaneously pressed to the proximal end to apply the compression force, and wherein both of the gripping portions are configured to be simultaneously released from the compressed state to release the compression force.

2. The steerable catheter according to claim 1, wherein the tube includes at least three wire lumens mutually spaced apart in a tube wall of the tube and extending from a proximal end section of the tube to a distal end section of the tube, and the operation means includes at least two wires, a first section of each of the at least two wires is individually inserted through one lumen of a pair of the wire lumens, an intermediate part of each of the at least two wires is folded over a distal end section of the second tube section, a second section of each of the at least two wires is individually inserted through another lumen of the pair of the wire lumens, and the first and second sections of each of the at least two wires reach a proximal end of the first tube section.

3. The steerable catheter according to claim 1, wherein the tube includes at least three wire lumens mutually spaced apart in a tube wall of the tube and extending from a proximal end section of the tube to a distal end section of the tube, and the operation means includes at least three wires, each of the at least three wires has a distal end connected to a distal end section of the second tube section, is inserted through one of the wire lumens, and has a proximal end reaching a proximal end of the first tube section.

4. The steerable catheter according to claim 1, wherein the operation means includes at least two wires, wherein the operating means is configured to selectively pull a first wire of the at least two wires, a second wire of the at least two wires, or both the first wire and the second wire of the at least two wires simultaneously, and wherein the operating means is further configured to:

exert the deflection force on the second tube section to deflect the second tube section in a first direction by pulling the first wire of the at least two wires, exert the deflection force on the second tube section to deflect the second tube section in a second direction, different from the first direction, by pulling the second wire of the at least two wires, or exert the compression force on the second tube section by pulling both the first wire and the second wire of the at least two wires simultaneously.

* * * * *